US00PP35337P2

(12) United States Plant Patent
Rinehart

(10) Patent No.: US PP35,337 P2
(45) Date of Patent: Aug. 22, 2023

(54) POINSETTIA PLANT NAMED 'RINE 19806'

(50) Latin Name: ***Euphorbia pulcherrima* Willd.**
Varietal Denomination: RINE 19806

(71) Applicant: Steven Earl Rinehart, Encinitas, CA (US)

(72) Inventor: Steven Earl Rinehart, Encinitas, CA (US)

( * ) Notice: Subject to any disclaimer, the term of this patent is extended or adjusted under 35 U.S.C. 154(b) by 0 days.

(21) Appl. No.: 18/087,361

(22) Filed: Dec. 22, 2022

(51) Int. Cl.
*A01H 5/00* (2018.01)
*A01H 6/38* (2018.01)

(52) U.S. Cl.
USPC ..... Plt./307

(58) Field of Classification Search
USPC ..... Plt./307
CPC ... A01H 5/00; A01H 5/02; A01H 6/38; A01H 6/385
See application file for complete search history.

(56) References Cited

U.S. PATENT DOCUMENTS

PP12,846 P2 * 8/2002 Fruehwirth ..... A01H 6/38 Plt./307

* cited by examiner

*Primary Examiner* — June Hwu
(74) *Attorney, Agent, or Firm* — C. Anne Whealy

(57) ABSTRACT

A new and distinct cultivar of Poinsettia plant named 'Rine 19806', characterized by its upright to slightly outwardly and uniformly mounded plant habit; moderately vigorous to vigorous growth habit; freely and upright to slightly outwardly branching habit; very thick lateral branches; strong upright "v-shape" branching habit; strongly upright dark green-colored leaves; upright flower bracts that are bright red in color; distinct, large and dense cyathia clusters; and good post-production longevity.

3 Drawing Sheets

Figure 1:
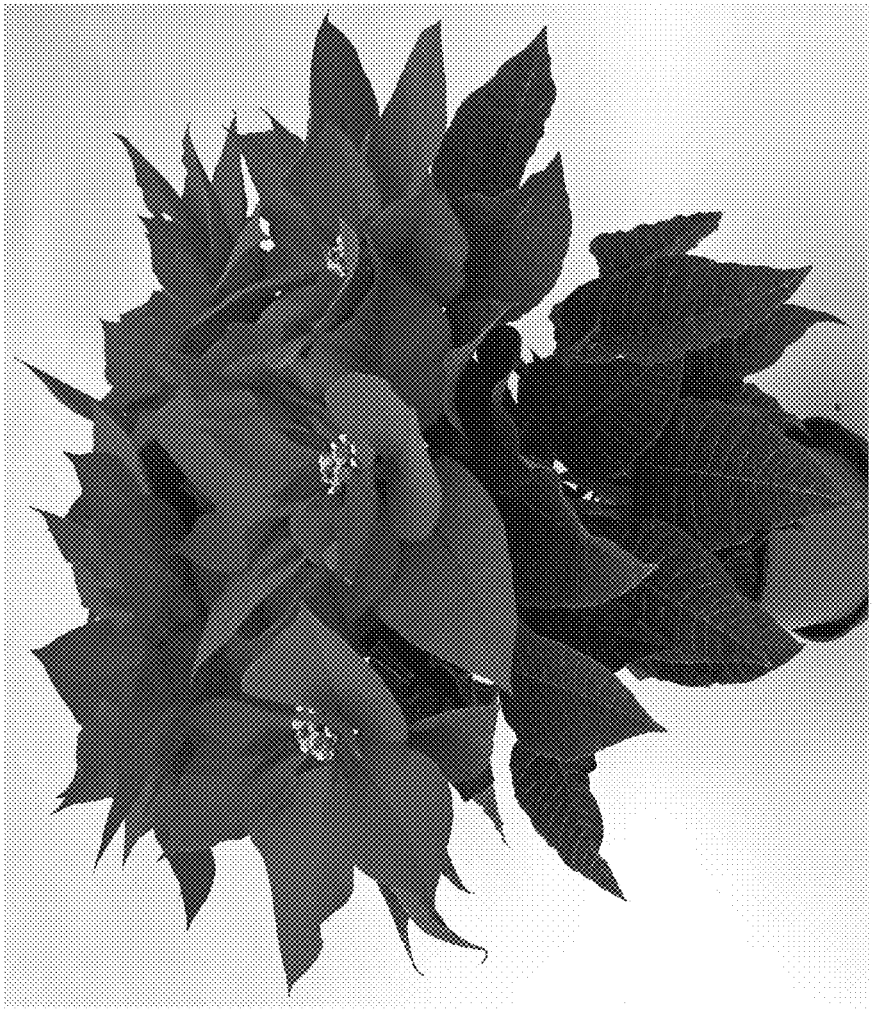

Botanical designation: *Euphorbia pulcherrima* Willd.
Cultivar denomination: 'RINE 19806'.

BACKGROUND OF THE INVENTION

The present invention relates to a new and distinct cultivar of Poinsettia plant, botanically known as *Euphorbia pulcherrima* Willd., and hereinafter referred to by the cultivar name 'Rine 19806'.

The new Poinsettia plant is a product of a planned breeding program conducted by the Inventor in Encinitas, Calif. The objective of the breeding program is to create new upright Poinsettia plants with upright leaves, upright flower bracts and excellent post-production longevity.

The new Poinsettia plant originated from a cross-pollination made by the Inventor in January, 2019 of *Euphorbia pulcherrima* Willd. 'Rineab', disclosed in U.S. Plant Pat. No. 32,593, as the female, or seed, parent, with *Euphorbia pulcherrima* Willd. 'Dueferra', disclosed in U.S. Plant Pat. No. 29,225, as the male, or pollen, parent. The new Poinsettia plant was discovered and selected by the Inventor as a single flowering plant from within the progeny of the stated cross-pollination in a controlled greenhouse environment in Encinitas, Calif. in November, 2019.

Asexual reproduction of the new Poinsettia plant by terminal vegetative cuttings in a controlled greenhouse environment in Encinitas, Calif. since April, 2019 has shown that the unique features of this new Poinsettia plant are stable and reproduced true to type in successive generations of asexual reproduction.

SUMMARY OF THE INVENTION

Plants of the new Poinsettia have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'Rine 19806'. These characteristics in combination distinguish 'Rine 19806' as a new and distinct Poinsettia plant:

1. Upright to slightly outwardly and uniformly mounded plant habit.
2. Moderately vigorous to vigorous growth habit.
3. Freely and upright to slightly outwardly branching habit; very thick lateral branches; strong upright "v-shape" branching habit.
4. Strongly upright dark green-colored leaves.
5. Upright flower bracts that are bright red in color.
6. Distinct, large and dense cyathia clusters.
7. Good post-production longevity.

In side-by-side comparisons, plants of the new Poinsettia differ primarily from plants of the female parent, 'Rineab', in the following characteristics:

1. Branching habit of plants of the new Poinsettia is stronger and more upright than branching habit of plants of 'Rineab'.
2. Lateral branches of plants of the new Poinsettia are darker green in color than lateral branches of plants of 'Rineab'.
3. Leaves of plants of the new Poinsettia are smaller and darker green in color than leaves of plants of 'Rineab'.
4. Leaves and flower bracts of plants of the new Poinsettia are more upright than and not as lobed as leaves and flower bracts of plants of 'Rineab'.

5. Flower bracts of plants of the new Poinsettia are brighter and darker red in color than flower bracts of plants of 'Rineab'.

In side-by-side comparisons, plants of the new Poinsettia differ primarily from plants of the male parent, 'Dueferra', in the following characteristics:

1. Flower bracts of plants of the new Poinsettia develop red coloration earlier than flower bracts of plants of 'Dueferra'.
2. Leaves and flower bracts of plants of the new Poinsettia are not as flat as leaves and flower bracts of plants of 'Dueferra'.
3. Flower bracts of plants of the new Poinsettia are more upright than flower bracts of plants of 'Dueferra'.
4. Flower bracts of plants of the new Poinsettia are lighter red in color than flower bracts of plants of 'Dueferra'.

Plants of the new Poinsettia can be compared to plants of the *Euphorbia pulcherrima* Willd. 'Eckadire', disclosed in U.S. Plant Pat. No. 12,846. In side-by-side comparisons, plants of the new Poinsettia differ primarily from plants of 'Eckadire' in the following characteristics:

1. Branching habit of plants of the new Poinsettia is more "v-shaped" than branching habit of plants of 'Eckadire'.
2. Lateral branches of plants of the new Poinsettia are thicker than lateral branches of plants of 'Eckadire'.
3. Leaves and flower bracts of plants of the new Poinsettia are more upright than leaves and flower bracts of plants of 'Eckadire'.
4. Flower bracts of plants of the new Poinsettia are lighter red in color than flower bracts of plants of 'Eckadire'.
5. Cyathia clusters of plants of the new Poinsettia are larger and more distinct than cyathia clusters of plants of 'Eckadire'.

Plants of the new Poinsettia can also be compared to plants of the *Euphorbia pulcherrima* Willd. 'PER1055', disclosed in U.S. Plant Pat. No. 15,882. In side-by-side comparisons, plants of the new Poinsettia differ primarily from plants of 'PER1055' in the following characteristics:

1. Branching habit of plants of the new Poinsettia is more uniform than branching habit of plants of 'PER1055'.
2. Flower bracts of plants of the new Poinsettia are not as wavy as flower bracts of plants of 'PER1055'.
3. Flower bracts of plants of the new Poinsettia are less prone to curve downwardly with development whereas flower bracts of plants of 'PER1055' curve downwardly with development.

BRIEF DESCRIPTION OF THE PHOTOGRAPHS

The accompanying photographs illustrate the overall appearance of the new Poinsettia plant showing the colors as true as it is reasonably possible to obtain in colored reproductions of this type. Colors in the photographs may differ slightly from the color values cited in the detailed botanical description which accurately describe the colors of the new Poinsettia plant.

The photograph on the first sheet (FIG. 1) is a side perspective view of a typical flowering plant of 'Rine 19806' grown in a container.

Figure 2:
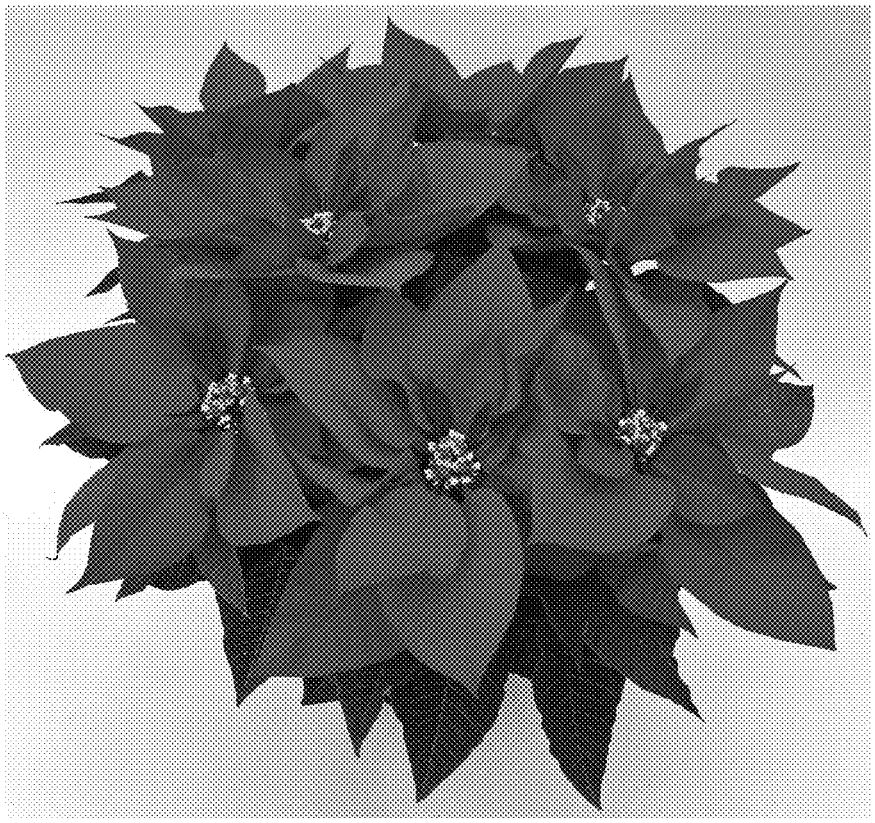

The photograph on the second sheet (FIG. 2) is a top perspective view of a typical flowering plant of 'Rine 19806'.

Figure 3:
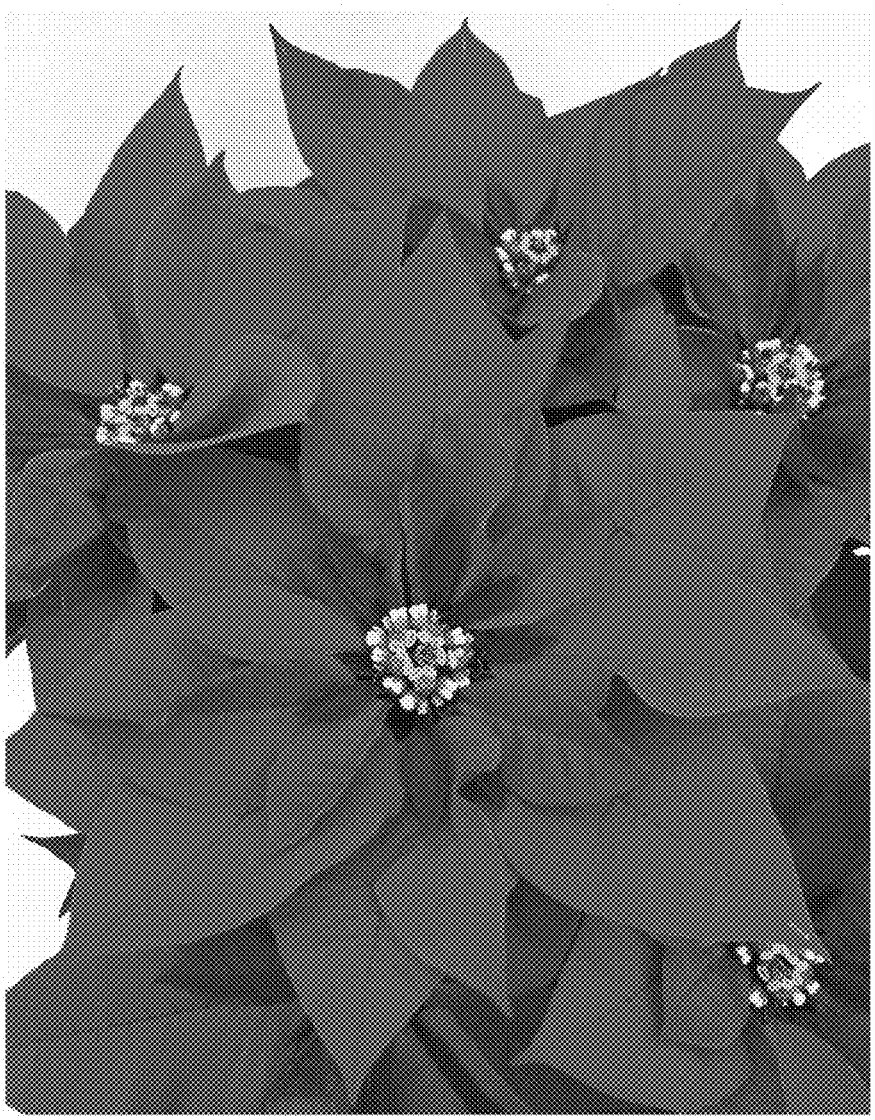

The photograph on the third sheet (FIG. 3) is a close-up view of a typical flowering plant of 'Rine 19806'.

DETAILED BOTANICAL DESCRIPTION

Plants used in the aforementioned photographs and in the following detailed description were grown during the autumn and winter in 15.24-cm containers in a polyethylene-covered greenhouse in Elfin Forest, Calif. under natural season conditions and cultural practices typical of commercial Poinsettia production. During the production of the plants, day temperatures ranged from 24° C. to 26° C., night temperatures averaged 18° C. and light levels ranged from 5,000 to 6,000 foot-candles. Plants were pinched one time and were five months from unrooted cuttings when the photographs and the description were taken. In the following description, color references are made to The Royal Horticultural Society Colour Chart, 2015 Edition, except where general terms of ordinary dictionary significance are used.

Botanical classification: *Euphorbia pulcherrima* Willd. 'Rine 19806'.

Parentage:

*Female, or seed, parent.*—*Euphorbia pulcherrima* Willd. 'Rineab', disclosed in U.S. Plant Pat. No. 32,593.

*Male, or pollen, parent.*—*Euphorbia pulcherrima* Willd. 'Dueferra', disclosed in U.S. Plant Pat. No. 29,225.

Propagation:

*Type.*—Terminal vegetative cuttings.

*Time to initiate roots, summer.*—About ten days at temperatures about 21° C.

*Time to initiate roots, winter.*—About ten days at temperatures about 19° C.

*Time to produce a rooted young plant, summer.*—About 26 days at temperatures about 21° C.

*Time to produce a rooted young plant, winter.*—About 28 days at temperatures about 19° C.

*Root description.*—Medium in thickness, fibrous; typically white in color, actual color of the roots is dependent on substrate composition, water quality, fertilizer type and formulation, substrate temperature and physiological age of roots.

*Rooting habit.*—Freely branching; medium density.

Plant description:

*Plant and growth habit.*—Upright to slightly outwardly spreading and uniformly mounded plant habit; broad inverted triangle; inflorescences with numerous flower bracts positioned above the foliar plane; moderately vigorous to vigorous growth habit and moderate growth rate.

*Plant height.*—About 38 cm.

*Plant diameter or spread.*—About 45 cm.

*Lateral branch description.*—Branching habit: Freely branching habit, about eight lateral branches develop after pinching; upright to slightly outwardly branching habit; strong upright "v-shaped" branching habit. Length: About 31 cm. Diameter: Thick, about 8.5 mm. Internode length: About 1.5 cm to 1.75 cm. Strength: Strong. Aspect: About 20° to 30° from vertical. Texture and luster: Smooth, glabrous; glossy. Color: Close to 146A and 146B.

*Leaf description.*—Arrangement: Alternate, simple. Length: About 12.5 cm. Width: About 8.5 cm. Shape: Broadly ovate, not lobed. Apex: Acuminate. Base:

Obtuse with truncate or cordate tendencies. Margin: Entire. Aspect: Mostly upright and becoming closer to horizontal with subsequent development. Texture and luster, upper surface: Smooth, glabrous; velvety; slightly glossy. Texture and luster, lower surface: Glabrous; prominent venation; somewhat velvety; matte. Venation pattern: Pinnate, arcuate. Color: Developing and fully expanded leaves, upper surface: Darker green than between 147A and N189A; midvein, close to 59A and lateral venation, close to 147A. Developing and fully expanded leaves, lower surface: Close to 147B; midvein, close to 59A and lateral venation, close to 146A to 146B. Leaf petioles: Length: About 4.3 cm. Diameter: Thick, about 4 mm. Texture and luster, upper and lower surfaces: Smooth, glabrous; glossy. Color, upper and lower surfaces: Close to 59A and 59B.

Inflorescence description:

*Inflorescence type and habit*.—Terminal inflorescences are compound corymbs of cyathia with numerous colored flower bracts subtending the cyathia; inflorescences uniformly positioned above the foliar plane.

*Fragrance*.—None detected.

*Flowering response*.—Under natural season conditions, plants typically flower about 56 days after planting rooted cuttings in Southern California.

*Post-production longevity*.—Good post-production longevity; plants of the new Poinsettia maintain good substance and flower bract color for about six weeks under interior conditions; flower bracts persistent and cyathia not persistent.

*Inflorescence diameter*.—About 27 cm to 30 cm.

*Inflorescence height* (*depth*).—About 7.25 cm.

*Flower bracts*.—Quantity per inflorescence: Numerous, about 30 to 40. Length, largest bracts: About 11.5 cm to 12.5 cm. Width, largest bracts: About 7.75 cm to 8.25 cm. Shape: Broadly ovate, not lobed. Apex: Acuminate. Base: Obtuse with truncate tendencies. Margin: Entire. Aspect: Upright presentation. Texture and luster, upper surface: Smooth, glabrous; velvety; matte. Texture and luster, lower surface: Glabrous with prominent venation; somewhat velvety; matte. Venation pattern: Pinnate, arcuate. Color: Transitional bracts, upper surface: Close to 146A and 147A variably tinged with close to N45A. Transitional bracts, lower surface: Close to 146A and 146B slightly and variably tinged with close to N45B. Developing and fully developed bracts, upper surface: Close to N45A; venation, close to N45A; color does not change with subsequent development. Developing and fully developed bracts, lower surface: Close to N45B; venation, close to N45B; color does not change with subsequent development. Bract petioles: Length: About 3.25 cm. Diameter: About 3 mm by 3.25 mm. Texture and luster, upper and lower surfaces: Smooth, glabrous; glossy. Color, upper and lower surfaces: Close to 59A to 59B.

*Cyathia*.—Quantity per corymb: About 17 to 20; relatively large and showy. Length: About 1.4 cm. Width: About 6 mm. Shape: Oblong. Texture and luster: Smooth, glabrous; slightly glossy. Color, inner surface: Close to 146B to 146C. Color, outer surface: Close to 144A to 144B; towards the apex, close to 53A.

*Nectaries*.—Quantity per cyathium: Two. Length: About 8 mm. Width: About 4 mm. Shape: Flattened tubular. Texture and luster: Smooth, glabrous; slightly glossy. Color, inner and outer surfaces: Close to 13A.

*Peduncles*.—Length: About 5 mm to 6 mm. Diameter: About 4 mm. Strength: Strong, thick. Aspect: Mostly upright to slightly outwardly. Texture and luster: Smooth, glabrous; slightly glossy. Color: Close to 144A to 144B.

*Reproductive organs*.—Stamens: Quantity per cyathium: About 16 to 20. Filament length: About 6 mm to 7 mm. Filament color: Close to 154D. Anther shape: Round to oval; bi-lobed. Anther length: About 1.25 mm. Anther color: Close to 13A. Amount of pollen: Scarce to moderate. Pollen color: Close to 13A. Pistils: Quantity per cyathium: One; tri-parted. Pistil length: About 9 mm. Stigma shape: Three-parted, recurved. Stigma color: Close to 144A. Style length: About 7.5 mm. Style color: Close to 154D. Ovary color: Close to 144D.

*Seeds and fruits*.—To date, seed and fruit production have not been observed on plants of the new Poinsettia.

Pathogen & pest resistance: To date, plants of the new Poinsettia have been observed to be relatively resistant to *Botrytis*. Plants have not been shown to be resistant to pests and other pathogens common to Poinsettia plants.

Temperature tolerance: Plants of the new Poinsettia have been observed to tolerate temperatures ranging from about 15° C. to about 32° C.

It is claimed:

1. A new and distinct Poinsettia plant named 'Rine 19806' as illustrated and described.

* * * * *